United States Patent
White

(10) Patent No.: US 10,765,414 B2
(45) Date of Patent: Sep. 8, 2020

(54) SEALING MECHANISM FOR CLOSURE DEVICES

(71) Applicant: TERUMO PUERTO RICO, L.L.C., Caguas, PR (US)

(72) Inventor: Troy T. White, Maple Grove, MN (US)

(73) Assignee: TERUMO PUERTO RICO, L.L.C., Caguas, PR (US)

( * ) Notice: Subject to any disclaimer, the term of this patent is extended or adjusted under 35 U.S.C. 154(b) by 75 days.

(21) Appl. No.: 15/269,814

(22) Filed: Sep. 19, 2016

(65) Prior Publication Data

US 2017/0007220 A1    Jan. 12, 2017

Related U.S. Application Data

(62) Division of application No. 13/590,722, filed on Aug. 21, 2012, now Pat. No. 9,468,429.

(51) Int. Cl.
  *A61B 17/00*      (2006.01)

(52) U.S. Cl.
  CPC .............. *A61B 17/0057* (2013.01); *A61B 2017/00004* (2013.01); *A61B 2017/00619* (2013.01);
(Continued)

(58) Field of Classification Search
  CPC ...... A61B 17/0057; A61B 2017/00575; A61B 2017/00004; A61B 2017/00619; A61B 2017/00628
  See application file for complete search history.

(56) References Cited

U.S. PATENT DOCUMENTS

| 5,053,046 A | 10/1991 | Janese |
| 6,045,569 A | 4/2000 | Kensey et al. |

(Continued)

FOREIGN PATENT DOCUMENTS

| EP | 2145585 A2 | 1/2010 |
| WO | 9831286 A1 | 7/1998 |
| WO | 2005006990 A2 | 1/2005 |

OTHER PUBLICATIONS

PCT Communication Relating to the Result of the Partial International Search for PCT International Application No. PCT/US2013/051059 dated Jan. 8, 2014 (2 pp.).

*Primary Examiner* — Thomas Mcevoy
(74) *Attorney, Agent, or Firm* — Buchanan Ingersoll & Rooney PC

(57) ABSTRACT

A deployment device for bringing a sealing plug into position within a puncture tract or incision, and bringing an anchor into position adjacent a tissue puncture, is provided. The deployment device is designed to facilitate easier positioning of the sealing plug, wherein a separate tamping tool is not required. The sealing plug is held in place on the shaft of the anchor by a structure, for example, a knob or boss. The anchor, anchor shaft, and sealing plug may be made of various biocompatible resorbable materials such that the anchor may resorb very quickly, leaving the tissue or artery lumen clear, and the sealing plug may resorb more slowly, to assist in maintaining hemostasis. The deployment device may include a bypass device which maintains the anchor in either an extended or bent configuration. Further, the anchor may include at least one rib, to provide support to the anchor.

12 Claims, 15 Drawing Sheets

(52) U.S. Cl.
CPC ............... *A61B 2017/00623* (2013.01); *A61B 2017/00628* (2013.01); *A61B 2017/00654* (2013.01); *A61B 2017/00659* (2013.01)

(56) References Cited

U.S. PATENT DOCUMENTS

| | | |
|---|---|---|
| 6,090,130 A | 7/2000 | Nash et al. |
| 7,618,436 B2 | 11/2009 | Forsberg |
| 7,749,248 B2 | 9/2010 | White et al. |
| 7,837,705 B2 | 11/2010 | White et al. |
| 7,931,670 B2 | 4/2011 | Fiehler et al. |
| 2003/0078616 A1 | 4/2003 | Ginn et al. |
| 2005/0149117 A1 | 7/2005 | Khosravi et al. |
| 2006/0047313 A1* | 3/2006 | Khanna .............. A61B 17/0057 606/232 |
| 2006/0099238 A1 | 5/2006 | Khosravi et al. |
| 2007/0276433 A1 | 11/2007 | Huss |
| 2010/0067854 A1 | 4/2010 | Stopek et al. |
| 2012/0010634 A1 | 1/2012 | Crabb et al. |
| 2012/0035644 A1 | 2/2012 | Eskaros et al. |

* cited by examiner

SEALING MECHANISM FOR CLOSURE DEVICES

RELATED APPLICATION

This is a divisional of U.S. patent application Ser. No. 13/590,722, filed on 21 Aug. 2012, now pending, the disclosure of which is incorporated, in its entirety, by this reference.

FIELD OF THE DISCLOSURE

This disclosure relates generally to medical devices and more particularly to tools for sealing punctures or incisions in a tissue wall.

BACKGROUND

Various surgical procedures are routinely carried out intravascularly or intraluminally. For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., a catheter) may pass through the sheath and to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices, such as those described in U.S. Pat. Nos. 6,045,569; 6,090,130; 7,618,436; 7,749,248; 7,837,705; 7,931,670, and related patents and patent applications, all of which are hereby incorporated by reference.

Typical closure tools or devices such as the ones described in the above-mentioned patents and patent applications place a sealing plug at one side of the tissue puncture site and an anchor on the other side of the tissue puncture site. Successful deployment of the sealing plug requires that it be ejected from within a device sheath or carrier tube into the incision or puncture tract and tamped down to an outer surface of the tissue puncture using a tamping tube (also called a compaction tube). The carrier tube extends from the proximal end to the distal end of the closure tool and includes an outlet at the distal end. The carrier tube may be made of plastic or other material and is designed for insertion through a sheath, and the sheath is designed for insertion through a percutaneous incision in a tissue layer and into a lumen. The sealing plug is initially disposed within the carrier tube, prior to deployment, and the anchor is positioned axially along the carrier tube. When the carrier tube is pulled away from the sealing plug and anchor, after the anchor has been positioned, for example, in a lumen, the sealing plug is deployed into the puncture tract. The carrier tube also houses a tamping device within, and the tamping device advances the sealing plug towards the anchor.

In a manually operated tool, the tamping procedure cannot commence until the carrier tube (within which the tamping device, such as a tamping tube, is located) has been removed so as to expose the tamping tube for manual grasping. The tamping tube is manually grasped and tamped against the sealing plug, setting the sealing plug within the incision or puncture tract, against an outer surface of the tissue puncture. In an automatic tamping system, the closure tool may have an automatic driving mechanism for automatically tamping the sealing plug within the incision or puncture tract toward the outer surface of the tissue puncture. The closure tool may have a tamping tube or tamping rack disposed adjacent to the sealing plug, such that the tamping tube or rack is driven by the automatic driving mechanism to tamp the sealing plug into the desired placement.

As noted above, once the anchor is anchored within the artery at the puncture site, further retraction of the closure tool and insertion sheath causes the sealing plug to withdraw from the distal end of the carrier tube, thereby depositing the plug within the incision or puncture tract. Improper positioning of the sealing plug, or shifting of the sealing plug, could result in poor sealing of the tissue puncture or incision, leading to body fluid leakage. Further, there is the potential that the anchor could loosen and at least partially obstruct the lumen, which could lead to body fluid leakage of the tissue puncture or incision. Therefore, there is a need for a tissue puncture closure tool that provides an improved anchor and sealing plug configuration that facilitates ease of deployment and secure positioning of the sealing plug, especially once the anchor is largely or completely resorbed.

SUMMARY

In one of the many possible embodiments, the present disclosure provides a deployment device for bringing a sealing plug into position within a puncture tract or incision, and deploying the sealing plug within the incision or puncture tract, towards the outer surface of a tissue puncture. The deployment device also deploys an anchor within a lumen at the inner surface of a tissue puncture. The anchor and the sealing plug are configured such that the sealing plug is held and maintained in position on a shaft connected to the anchor, thereby not requiring any tamping to dispose the sealing plug into position within the puncture tract.

According to one aspect of the disclosure, an anchor assembly comprises an anchor, an anchor shaft, and a knob, boss, or similar protuberance, disposed on the proximal end of the anchor shaft. Going forward, the term "boss" is used as representative of a knob, projection or other protuberance. The sealing plug material is mounted onto the anchor shaft such that the anchor boss holds and maintains the sealing plug material in place. Further, the anchor boss restricts movement of the sealing plug proximally in the carrier tube. The anchor assembly and the sealing plug are made of biocompatible resorbable materials, but are not all required to be made of the same biocompatible resorbable material. For example, the anchor may be made of material that resorbs more quickly than the material composing the sealing plug.

In another aspect of the disclosure, the anchor comprises at least one rib, and preferably a plurality of ribs. The anchor is made of semi-flexible or flexible material. Further, the ribs are made of biocompatible resorbable flexible or semi-flexible material. The anchor is configured such that the anchor, with or without at least one rib, is bendable or foldable, and yet has shape memory and may return to its original shape.

According to yet another aspect of the disclosure, the tissue puncture closure device comprises a carrier tube; a bypass device wherein the bypass device is disposed on the distal end of the carrier tube; an anchor assembly comprising an anchor, an anchor shaft, and boss disposed on the proximal end of the anchor shaft, the anchor assembly disposed in the interior lumen of the bypass device; a sealing plug disposed in the distal end portion of the carrier tube; a suture coupled to the anchor shaft and threaded proximally through the sealing plug material; and a cap disposed at the proximal end of the tissue puncture closure device wherein the proximal end of the suture is coupled to the cap.

According to yet another aspect of the disclosure, the tissue puncture closure device comprises a carrier tube wherein the distal portion of the carrier tube includes a shoulder or other obstruction emanating from the interior wall of the carrier tube; a sealing plug disposed in the distal end portion of the carrier tube, wherein the shoulder or other obstruction maintains the sealing plug in the distal portion of the carrier tube; an anchor assembly comprising an anchor, an anchor shaft, and knob or boss disposed on the proximal end of the anchor shaft, the anchor assembly disposed in the interior lumen of a bypass device and at the distal end of the carrier tube; and a suture coupled to the anchor shaft, threaded proximally through the sealing plug material and coupled to a cap disposed at the proximal end of the tissue puncture closure device.

In yet another aspect of the disclosure, the tissue puncture closure device comprises a carrier tube wherein the distal portion of the carrier tube includes a shoulder or other obstruction emanating from the interior wall of the carrier tube. In one aspect of the disclosure, the inner diameter of the lumen of the distal portion of the carrier tube is greater than the inner diameter of the lumen of the proximal portion of the carrier tube. In yet another aspect of the disclosure, the inner diameter of the lumen of the distal portion of the carrier tube is substantially the same as the inner diameter of the lumen of the proximal portion of the carrier tube.

According to yet another aspect of the disclosure there is disclosed a method of closing or sealing a tissue puncture wherein the tissue puncture closure device is inserted through an insertion sheath (or directly) and into the tissue puncture, the anchor is deployed within the tissue or vessel lumen, the tension on the suture is increased such that the anchor shaft is drawn proximally through the sealing plug material and the sealing plug material is mounted on the anchor shaft and held there by the anchor shaft boss as the anchor is disposed adjacent the inner wall of the tissue puncture or vessel, the tissue puncture closure device and insertion sheath are removed from the tissue puncture tract as a unit, deploying the sealing plug in the puncture tract, and the suture is released from the cap.

One skilled in the art would understand that the various aspects of the present disclosure described above may be combined and intermixed into various other arrangements and combinations, to achieve the desired performance of a tissue puncture closure device and desired sealing of a tissue puncture, especially as related to varying the rates of resorbtion of the anchor and sealing plug.

The above summary of the various representative embodiments of the disclosure is not intended to describe each illustrated embodiment or every implementation of the disclosure. Rather, the embodiments are chosen and described to that others skilled in the art may appreciate and understand the principles and practices of the disclosure. The figures in the detailed description that follows more particularly exemplify these embodiments.

BRIEF DESCRIPTION OF THE DRAWINGS

These as well as other objects and advantages of this disclosure will be more completely understood and appreciated by referring to the following more detailed description of the example embodiments of the disclosure in conjunction with the accompanying drawings of which.

Figure 1:
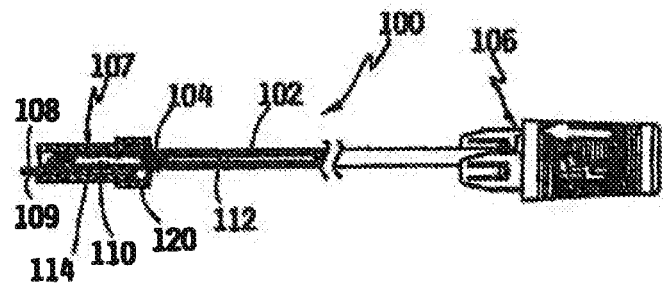
FIG. 1 is a side view, partly in section, of an internal tissue puncture closure tool.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the disclosure is to cover all modifications, equivalents, and alternatives.

DETAILED DESCRIPTION

As mentioned above, vascular procedures are conducted throughout the world and require access to an artery through a puncture. Most often, the artery is a femoral artery. To close the puncture following completion of the procedure, many times a closure tool is used to sandwich the puncture between an anchor and a sealing plug. However, it is preferred that the anchor, which is generally located at the puncture or incision, for example, in the femoral artery, reabsorb quickly, thereby providing an unobstructed blood vessel lumen. The present disclosure describes devices and methods to facilitate the closure of the puncture or incision, and the maintenance of hemostasis by the temporary anchor, and the sealing plug which is placed within the incision or puncture track. The method of deployment is simplified, using devices of the disclosure. The sealing plug and anchor may be made of various biocompatible resorbable materials, and are not required to be made of the same resorbable material. For example, the anchor may be made of DLPLA (poly(di-lactide)) and the sealing plug may be made of collagen. While the vascular instruments shown and described below include insertion sheaths and puncture sealing devices, the application of principles described herein are not limited to the specific devices shown. The principles described herein may be used with any vascular closure or similar tissue closure device. Further, the devices and methods described herein may be used to seal blood vessel punctures, as well as organ punctures.

As used in this specification and the appended claims, the term "carrier tube" is used broadly to mean any elongated device or series of devices, including any intermediate components, used alone or in combination to carry or transport at least a sealing plug, directly or indirectly. "Engage" and "engageable" are also used broadly to mean interlock, mesh, or contact between two devices. A "lumen" refers to any open space or cavity in a bodily organ or device, especially in a blood vessel. "Gradually" means advancing or progressing by regular or continuous degrees, or absent any abrupt changes. "Sudden" refers to a rapid, abrupt, or quick change. The words "including" and "having," as used in the specification, including the claims, have the same meaning as the word "comprising."

Referring now to the drawings, and in particular to FIGS. 1-4, a vascular puncture closure tool 100 is shown according to the prior art. The vascular puncture closure tool 100 includes a carrier tube 102 with a filament or suture 104 extending at least partially therethrough. The vascular puncture closure tool 100 also includes a first or proximal end 106 portion and a second or distal end portion 107. External to a distal end of the carrier tube 102 is an anchor 108. The anchor 108 is an elongated, stiff, low profile member including an eye 109 formed on the top surface, at approximately the middle, of the anchor 108. However, other shapes for the anchor 108 are possible. The anchor 108 is typically made of a biocompatible resorbable polymer.

The suture 104 is threaded through the anchor 108 and back to a bioresorbable sealing pad or plug; for example, a collagen plug 110. The collagen plug 110 may be comprised of randomly oriented fibrous material bound together by chemical means. The collagen plug 110 is slidingly attached to the suture 104 as the suture passes distally through the carrier tube 102 and, as the suture traverses the anchor 108 through the eye 109 and reenters the carrier tube 102, the suture 104 is securely slip knotted proximal to the collagen plug 110 to facilitate cinching of the collagen plug 110 when the vascular puncture closure tool 100 is properly placed and the anchor 108 has been deployed (see FIG. 4). The suture 104 may thus connect the anchor 108 and the collagen plug 110 in a pulley-like arrangement to cinch the anchor 108 and the collagen plug 110 together when the carrier tube 102 is pulled away from the anchor 108 and the collagen plug 110. The anchor 108 and the collagen plug 110 sandwich the tissue puncture therebetween, and lock together to seal the tissue puncture 118.

The carrier tube 102 typically includes a compaction device, tamping tube or compaction tube 112, disposed therein. The compaction tube 112 is slidingly mounted on the suture 104 and may be used by an operator to tamp the collagen plug 110 toward the anchor 108 at an appropriate time to seal a percutaneous tissue puncture.

Prior to deployment of the anchor 108 within an artery, the eye 109 of the anchor 108 rests outside the distal end portion 107 of the carrier tube 102. The anchor 108 may be temporarily held in place flush with the carrier tube 102 by a bypass tube 114 disposed over the distal end of the carrier tube 102.

Figure 2:
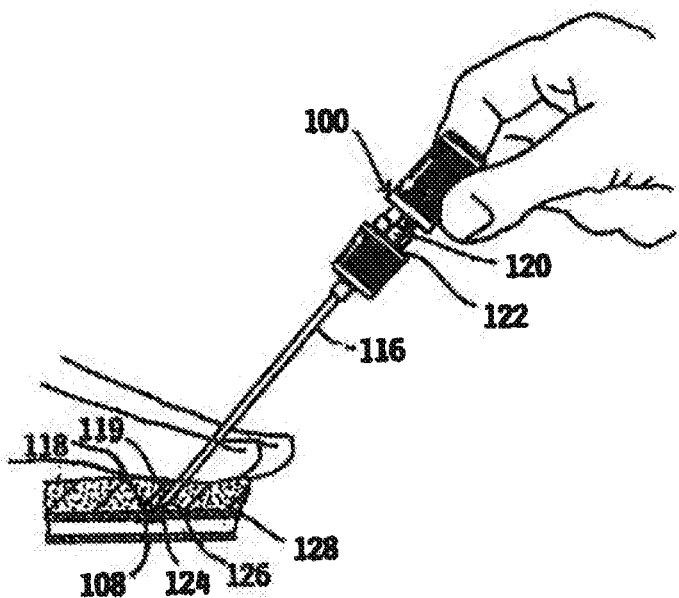
FIG. 2 is a side view of the tissue puncture closure tool of FIG. 1 inserted through an insertion sheath and engaged with an artery, the artery shown in section.
Figure 3:
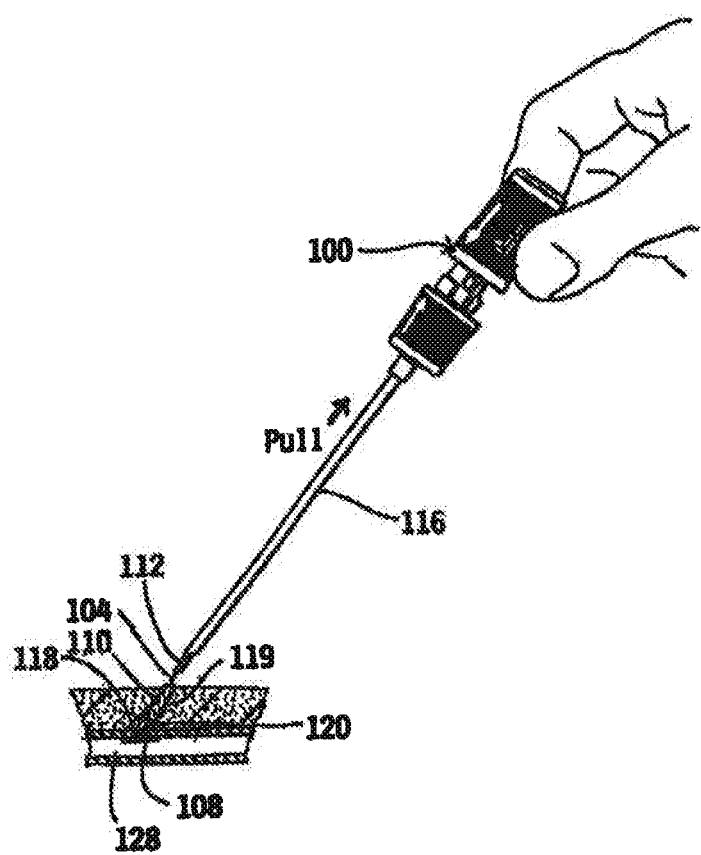
FIG. 3 is a side view of the tissue puncture closure tool, insertion sheath, and artery of FIG. 2, wherein the tissue closure tool and insertion sheath are being withdrawn from the artery to deploy a sealing plug, a collagen pad.
Figure 4:
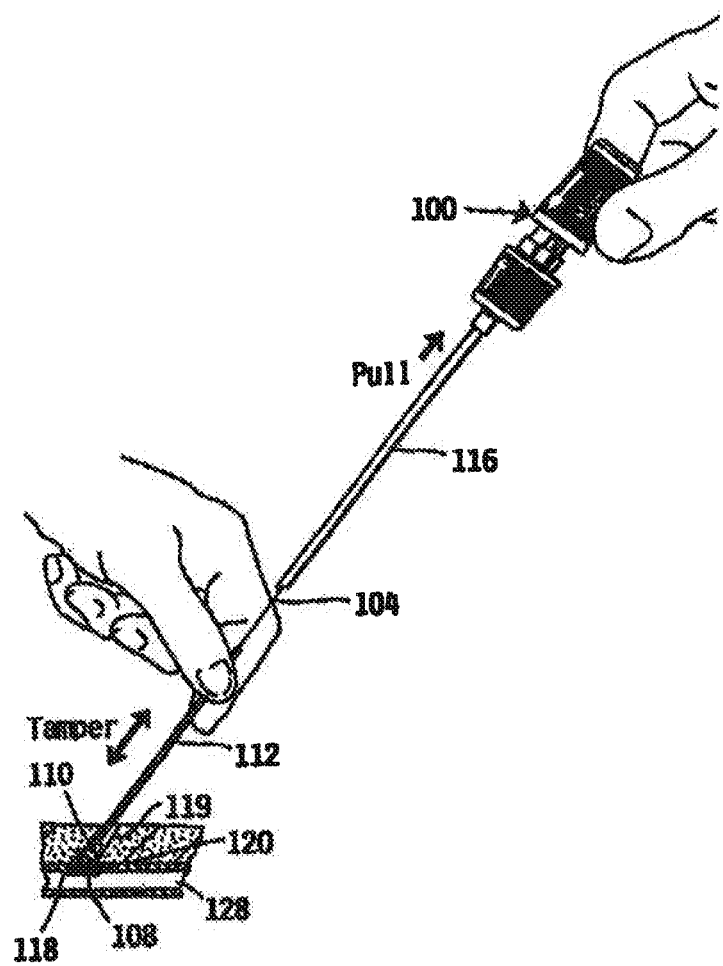
FIG. 4 is a side view of the tissue puncture closure tool, insertion sheath, and artery shown in FIG. 3 with a compaction device fully exposed and being used to tamp the collagen pad.

The flush arrangement of the anchor 108 and carrier tube 102 allows the anchor 108 to be inserted into an insertion sheath 116 as shown in FIGS. 2-4, and eventually through a tissue puncture 118. The insertion sheath 116 is shown in FIGS. 2-4 inserted through a percutaneous incision 119 (also referred to as an incision tract 119) and into an artery 128. The bypass tube 114 (FIG. 1) includes an oversized head 120 that prevents the bypass tube 114 from passing through an internal passage of the insertion sheath 116. Therefore, as the vascular puncture closure tool 100 is inserted into the insertion sheath 116, the oversized head 120 bears against a surface 122 of the insertion sheath 116. Further insertion of the vascular puncture closure tool 100 results in sliding movement between the carrier tube 102 (FIG. 1) and the bypass tube 114, releasing the anchor 108 from the bypass tube 114 (FIG. 1). However, the anchor 108 remains in the flush arrangement shown in FIG. 1 following release from the bypass tube 114 as the insertion sheath 116 continues to limit anchor 108 movement.

The insertion sheath 116 includes a monofold 124 at a second or distal end 126 thereof. The monofold 124 acts as a one-way valve to the anchor 108. The monofold 124 is a plastic deformation in a portion of the insertion sheath 116 that elastically flexes as the anchor 108 is pushed out through the distal end 126 thereof. Typically, after the anchor 108 passes through the distal end 126 of the insertion sheath 116 and enters the artery 128, the anchor 108 is no longer constrained to the flush arrangement with respect to the carrier tube 102 and the anchor 108 deploys and rotates to the position shown in FIG. 2.

Referring next to FIGS. 3-4, with the anchor 108 deployed, the vascular puncture closure tool 100 and the insertion sheath 116 are withdrawn together, forcing the collagen plug 110 through the tip of the carrier tube 102 and depositing it in the incision tract 119. The compaction tube 112 is also exposed. With the compaction tube 112 fully exposed as shown in FIG. 4, the compaction tube 112 is manually grasped, the collagen plug 110 is manually tamped, and the anchor 108 and collagen plug 110 are cinched together and held in place with the self-tightening slip-knot on the suture 104. Thus, the tissue puncture is sandwiched between the anchor 108 and the collagen plug 110, thereby sealing the tissue puncture 118. The suture 104 is then cut and the incision tract 119 may be closed. The suture 104, anchor 108, and collagen plug 110 are generally made of resorbable materials, and remain in place while the tissue puncture 118 heals, until the resorbable materials eventually resorb into the body.

Figure 5:
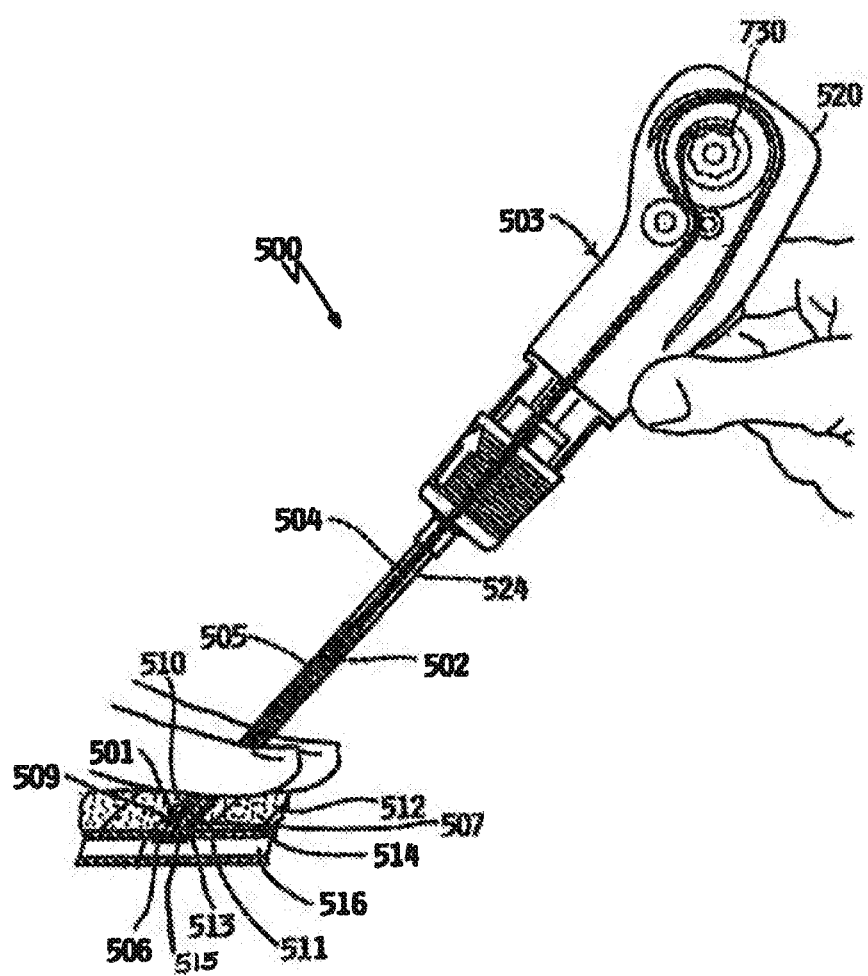
FIG. 5 is a side view of a tissue puncture closure tool with an automatic compaction mechanism shown engaged with an artery.
Figure 6:
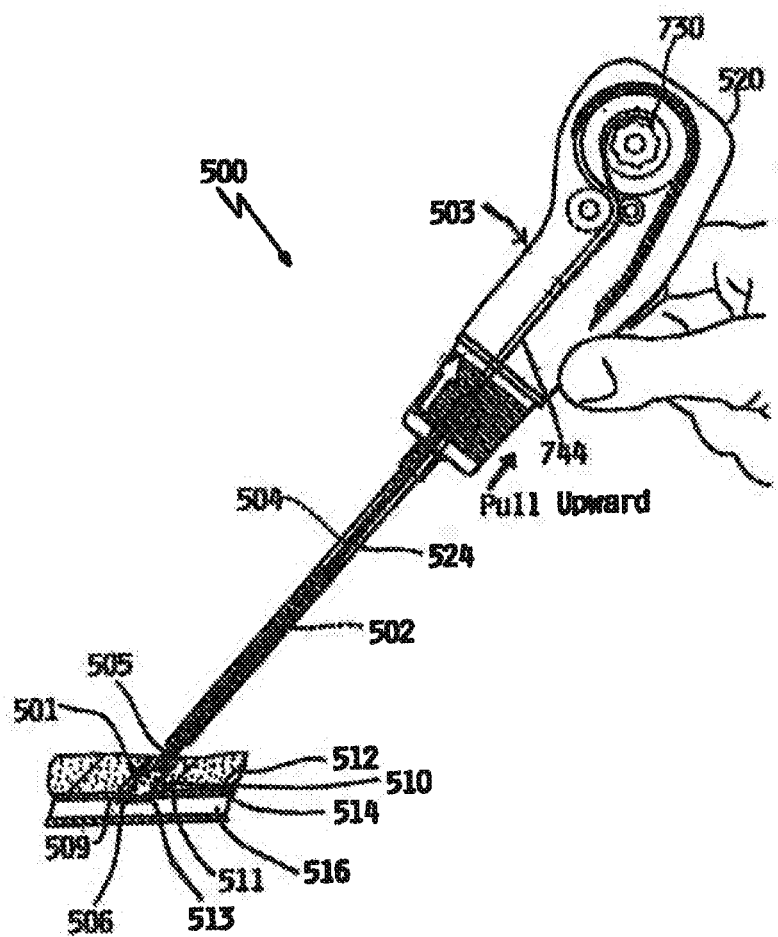
FIG. 6 is a side view of the tissue puncture closure tool of FIG. 5 being withdrawn from an artery

Referring to FIGS. 5 and 6, there is shown another vascular puncture closure tool. The tissue closure tool 500 includes a first or proximal end portion 503 and a second or distal end portion 507. A carrier tube 504 extends from the proximal end portion 503 to the distal end portion 507 and includes an outlet 515. The carrier tube 504 may be made of plastic or other material and is designed for insertion through a sheath 524 which is designed for insertion through a percutaneous incision 501 in a tissue layer 512 and into a lumen 516. According to FIG. 5, the blood vessel lumen 516 defines an interior surface of a femoral artery 514.

The distal end portion 507 of the carrier tube 504 also includes an anchor 506 and a sealing plug 510. The anchor 506, in this instance, is an elongated, stiff, low-profile member preferably made of a biologically resorbable polymer. The sealing plug 510 is formed of a compressible sponge or foam, made of a hemostatic biologically resorbable material such as collagen, and may be configured in any shape so as to seal the tissue puncture 513.

The sealing plug 510 and anchor 506 are connected to one another by a suture, thread, or filament 502 that is also biologically resorbable. The suture 502 extends distally from the first or proximal end portion 503 of the closure tool 500 through the carrier tube 504. The suture 502 is threaded through the sealing plug 510, then through an orifice (or orifices) in the anchor 506 and proximally back through the carrier tube 504 to the sealing plug 510. The suture 502 is preferably threaded through a perforation or series of perforations in the sealing plug 510. The suture 502 may also be threaded around itself to form a self-tightening slip-knot. The suture 502 thus connects the anchor 506 and the sealing plug 510 in a pulley-like arrangement that serves to cinch the anchor 506 and the sealing plug 510 together when the carrier tube 504 is pulled away from the anchor 506 and the sealing plug 510, sandwiching the tissue puncture therebetween, locking the anchor 506 and sealing plug 510 together and thereby sealing the tissue puncture 513.

The carrier tube 504 also includes a compaction device, such as a tamping tube or compaction tube 505, for tamping the sealing plug 510 along the suture 502 and against the anchor 506. The compaction tube 505 is shown located within the carrier tube 504 and proximal of the sealing plug 510. The compaction tube 505 is an elongated tubular member that may be rigid or flexible and formed of any suitable material. The suture 502 extends through the compaction tube 505 but is not directly connected thereto. Accordingly, the suture 502 and compaction tube 505 are free to slide past one another. According to the embodiment of FIG. 5, as the suture 502 extends beyond a proximal end of the compaction tube 505 and attaches to an automatic driving mechanism 730 located within a housing 520 at the first or proximal end portion 503 of the closure tool 500.

In practice, the carrier tube 504 of the closure tool 500 (containing the closure elements described above; the knot, suture, and the sealing plug; with the anchor positioned flush against the exterior of the carrier tube, held in position by a bypass tube) is inserted into an insertion sheath 524, which is already inserted within the artery 514. As the closure tool 500 and the associated closure elements are inserted into the insertion sheath 524, the anchor 506 passes through and out of a distal end 509 of the insertion sheath 524 and is inserted into the artery lumen 516. The closure tool 500 is then withdrawn from the insertion sheath 524 until the anchor 506 catches on the distal end 509 of the insertion sheath 524 and rotates to the position shown in FIG. 5. When resistance to further retraction of the closure tool 500 is felt by an operator, the closure tool 500 and the insertion sheath 524 are withdrawn together, causing the anchor 506 to anchor itself within the artery 514 against the artery wall 511. With the anchor 506 anchored within the artery 514 at the site of tissue puncture 513, further retraction of the closure tool 500 and insertion sheath 524 causes the sealing plug 510 to deploy from the distal end portion 507 of the carrier tube 504, thereby depositing the plug within the percutaneous incision or puncture tract 501.

However, unlike the initial closure tool described above, and similar such closure tools that require a separate, manual tamping procedure following the deposition of the sealing plug 510, closure tool 500 automatically tamps the sealing plug 510. The automatic driving mechanism 730 drives, via a rack or compaction tube driver 744, the compaction tube 505 toward the sealing plug 510 automatically upon withdrawal of the closure tool 500 from the percutaneous incision or puncture tract 501, tamping the sealing plug 510 toward the anchor 506 as shown in FIG. 6. The rack or compaction tube driver 744 may be coilable or may be a linear rack. The sealing plug 510 is tamped while the carrier tube 504 is still arranged adjacent to the tissue puncture 513 in the femoral artery 514, reducing or eliminating any gaps that may otherwise occur between the sealing plug 510 and the tissue puncture 513 in the femoral artery 514.

In addition, by placing tension on or pulling the suture 502 away from the puncture tract, the suture 502 cinches and locks (with a slip knot or the like) together the anchor 506 and the sealing plug 510, sandwiching the artery wall 511 between the anchor 506 and sealing plug 510. The force exerted by the compaction tube 505 and the cinching together of the anchor 506 and sealing plug 510 by the filament 502 also causes the sealing plug 510 to deform radially outward within the puncture tract and function as an anchor on the proximal side of the tissue puncture site 513.

The function of closure tools including the implementing principles described herein include closure of a percutaneous puncture or incision in tissue separating two internal portions of a living body, such as punctures or incisions in blood vessels, ducts or lumens, gall bladders, livers, hearts, etc.

As noted above, once the anchor is anchored within the blood vessel lumen, or organ lumen, at the puncture site, further retraction of the closure tool and insertion sheath causes the sealing plug to withdraw from the distal end of the carrier tube, thereby depositing the plug within the incision or puncture tract. Improper positioning of the sealing plug could result in poor sealing of the tissue puncture or incision, leading to body fluid leakage. Further, it is desirable for the anchor to reabsorb reasonably quickly so that the blood vessel or other lumen is clear, yet for the sealing plug to remain securely in place in the puncture tract or incision without being forced out of place by blood flow once the anchor is resorbed. Therefore, there is a need for a closure tool that provides an improved anchor and sealing plug configuration that facilitates ease of deployment and secure positioning of the sealing plug, especially once the anchor is largely or completely resorbed.

Figure 7:
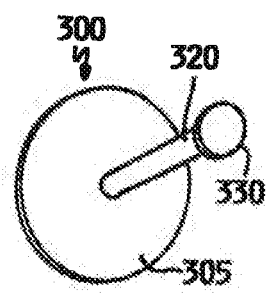
FIG. 7 is a perspective view of an anchor assembly according to one embodiment of the disclosure.
Figure 8:
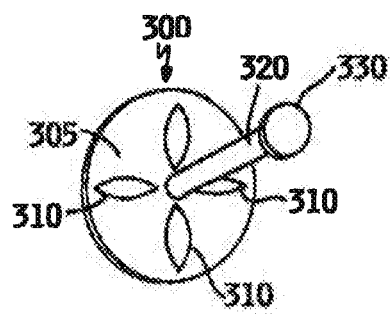
FIG. 8 is a perspective view of an anchor assembly with the anchor including a plurality of ribs according to one embodiment of the disclosure.
Figure 9:
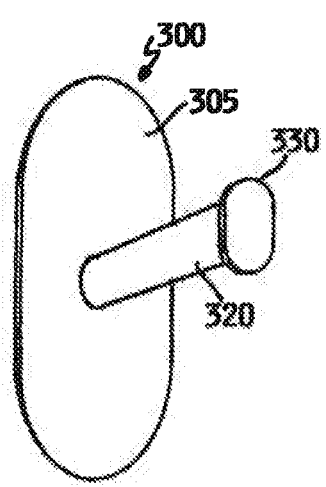
FIG. 9 is a perspective view of an anchor assembly with an anchor of an alternative shape according to one embodiment of the disclosure.
Figure 10:
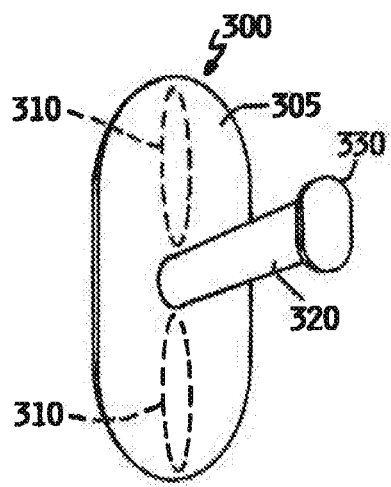
FIG. 10 is a perspective view of an anchor assembly with a plurality of ribs according to one embodiment of the disclosure.

Referring to FIGS. 7-10, there are shown examples of anchor assemblies 300 usable in sealing the puncture or incision. The devices and methods of the disclosure may be used for sealing various types of punctures and/or incisions, however, sealing a percutaneous puncture used to access the femoral artery is given as just a general example of such use. The anchor assembly 300 may comprise an anchor 305, an anchor shaft 320, and a knob or boss 330 on the proximal end of the anchor shaft 320. The anchor 305 may be a flexible or semi-flexible anchor 305, designed to conform to the interior wall of a puncture, for example, the interior wall of an artery, of an arteriotomy. The anchor 305 generally has a low profile, and may take on a variety of shapes, such as round, oval, or elliptical, for example. In one embodiment, the anchor 305 includes at least one semi-flexible rib, and preferably, a plurality of semi-flexible ribs 310, that add support to the anchor 305. However, the materials used to make the ribs 310 and the placement of the ribs 310 within a body of the anchor 305 still allow for the anchor 305 to retain its flexibility and to bend such that the anchor 305 may fit inside a deployment device. FIG. 7 shows one embodiment of an anchor 305, wherein the anchor 305 does not include supporting ribs 310. FIG. 8 shows another embodiment where the anchor 305 includes a plurality of ribs 310 placed along distinct radii, equidistantly spaced about the anchor 305. However, the ribs 310 are not required to be equidistantly spaced and may be spaced apart as desired, and still provide support, and the flexibility desired for the anchor 305 to be bendable and fit into a deployment device. Further, the number of ribs 310 may be decreased or increased, as desired. FIG. 9 shows another embodiment of a differently shaped anchor 305, wherein the anchor 305 also conforms to the interior of the arteriotomy. FIG. 10 shows another embodiment of an anchor 305, wherein the anchor 305 includes a plurality of ribs 310. The placement and number of the ribs 310 shown in the embodiments of the anchors 305 as shown in FIGS. 8 and 10 may be altered as desired. Further, other shapes for the anchor 305 and number and placement of the ribs 310 are contemplated. However, it is desired that the shape and size of the anchor 305 conform to and seal the particular tissue puncture, such as conforming to and sealing a puncture in an artery wall. The ribs 310 in any one anchor 305 may be flexible ribs 310, semi-flexible ribs 310, rigid ribs 310, or combinations thereof, dependent upon, for example, design and/or performance requirements, shape, deployment method and device, and positioning of the anchor 305. Further, the ribs 310 may take on various shapes, for example, elliptical, rectangular, and oval, as well as the aforementioned shapes, with narrow or tapered longitudinal ends. The at least one rib 310 may be disposed in the interior of the anchor 305, partially in the interior of the anchor 305, or on the surface of the anchor 305.

Figure 11:
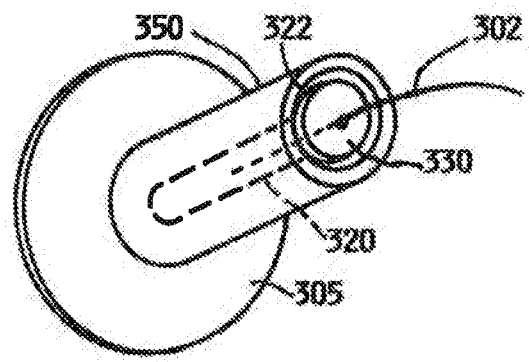
FIG. 11 is a perspective view of an anchor assembly with the sealing plug partially mounted on the anchor shaft, according to one embodiment of the disclosure.

Additionally, as shown in FIGS. 7-10, the anchor 305 includes an anchor shaft 320. The anchor shaft 320 may be semi-flexible or rigid. The anchor shaft 320 may be integrally formed with the anchor 305 or may be coupled with the anchor 305. The anchor shaft 320 includes a structure at the end of the anchor shaft 320, such as a projection, knob, boss or other protuberance 330. The knob or boss 330 of the anchor shaft 320 may also be semi-flexible or rigid. As noted above, the term "boss" is used to describe a protuberance, knob, or other knob-like projection 330 on the proximal end of the anchor shaft 320. The boss 330 may be integrally formed with the anchor shaft 320 or may be coupled to the anchor shaft 320. The boss 330 is configured such that a sealing plug 350 may be mounted on the anchor shaft 320 and, once mounted on the anchor shaft 320, the sealing plug 350 cannot be removed from the anchor shaft 320. The sealing plug 350 material is advanced distally over the boss 330, over the anchor shaft 320, towards the anchor 305. Once the sealing plug 350 material passes over the boss 330, the sealing plug 350 material cannot advance proximally back over the boss 330. FIG. 11 shows an embodiment of the anchor 305 with the sealing plug 350 material advancing over the anchor shaft 320, but not yet over the boss 330. The anchor assembly 300 also includes a filament, suture or thread 302 and the like, coupled to the anchor shaft 320. The term suture 302 is used hereinafter to encompass other like structures, for example, a thread or filament. The suture 302 is bioresorbable and is attached to the anchor shaft 320 by, for example, being tied to the anchor shaft 320, being molded into the anchor shaft 320, or the like. The anchor 305, anchor shaft 320, suture 302, ribs 310, and sealing plug 350 are all made of bioresorbable material, however, they do not need to all be made of the same bioresorbable material.

The anchor 305 may be made from a variety of bioresorbable materials, including but not limited to biodegradable flexible polyurethanes, DLPLA (poly(di-lactide)), LPLA (poly(l-lactide)), PGA (polyglycolide), PCL (poly(ε-caprolactone), PDO (poly(dioxanone)), PGA-PCL, PLA-PCL, PGA-TMC (poly(glycolide-co-trimethylene carbonate)), PGA-PCL-TMC (poly(glycolide-co-ε-caprolactone-co-trimethylene carbonate)), PLA-PCL-TMC (poly(lactide-co-ε-caprolactone-co-trimethylene carbonate)), PGA-LPLA (poly(1-lactide-co-glycolide)), PGA-DLPLA (poly(di-lactide-co-glycolide)), LPLA-DLPLA (poly(l-lactide-co-di-lactide)), PDO-PGA-TMC (poly(glycolide-co-trimethylene carbonate-co-dioxanone)), PHB (polyhydroxybutyrate), PHV (polyhydroxyvalerate), polyanhydrides (fast degrading), poly(orthoester), and the like. Generally, it is desirable that the anchor 305 resorb rather quickly, once deployed at the interior surface of the particular lumen or arteriotomy. The anchor 305 may be designed to resorb within 1 hour to about 90 days, dependent upon, for example, the choice of material for the anchor 305.

The anchor shaft 320, boss 330, and sealing plug 350 are also made of a bioresorbable material and may also be designed to resorb from within 1 day to about 90 days. The material of the sealing plug 350 may be chosen such that the sealing plug 350 material swells once the material contacts bodily fluids. The swelling of the material of the sealing plug 350 may assist in maintaining the sealing plug 350 in place in the puncture tract or incision, and may assist in creating hemostasis from outside the artery, or outside some other type of tissue puncture. The sealing plug 350 may be made from synthetic polymers or natural polymers. Materials for the sealing plug 350 include, but are not limited to, PAA (poly(acrylic acid) and PAAS (sodium polyacrylate), PEG (poly ethylene gluycol) or PEO (polyethylene oxide), PEG-PGA, PEG-PLA, PHEMA (poly(2-hydroxyethyl methacrylate)), PNIPAAm (poly(N-isopropyl acrylamide)), PVP (poly(N-vinyl pyrrolidine)), PVA (polyvinyl alcohol), PPF (poly(propylene fumarates)), hyaluronic acid (HA), alginic acid, dextran, chitosan, agarose, poly-L or D-lysine (PLL or PDL), cellulose, collagen, gelatin, and the like. The anchor shaft 320 and anchor boss 330 may be made of materials listed for the anchor 305 or the sealing plug 350, dependent upon the desired performance characteristics.

Figure 12:
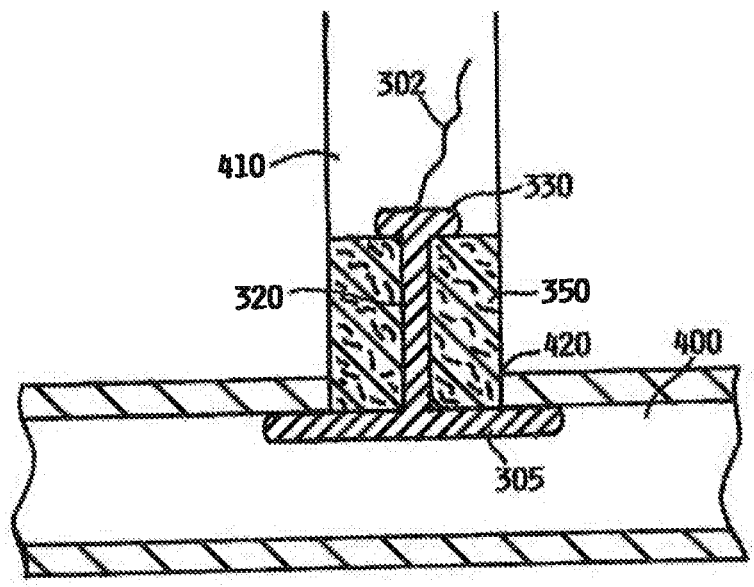
FIG. 12 is a side view of a tissue puncture with an anchor assembly and sealing plug deployed, according to one embodiment of the disclosure.

The anchor 305 may be deployed such that the anchor 305 conforms to the inner wall of a tissue puncture, for example, to the inner wall surface of a blood vessel, creating hemostasis from within the blood vessel or artery lumen. The sealing plug 350 is positioned in the puncture tract or incision, on the anchor shaft 320 of the anchor 305. The sealing plug 350 is in contact with the exterior surface of, for example, the arteriotomy, creating hemostasis from outside the artery. The anchor 305 may be designed to dissolve rapidly, in as little as 1 hour, leaving only the sealing plug 350, and perhaps the anchor shaft 320 and boss 330, in the puncture tract or incision to maintain hemostasis. Alternatively, the anchor 305 may be designed to dissolve less rapidly, based at least upon the material composing the anchor 305. FIG. 12 shows the anchor 305 in place in the lumen 400 of a vessel, sealing the tissue puncture 420. The sealing plug 350 is in place in the puncture tract 410, and is held in place by the boss 330 and the anchor 305.

Figure 13:
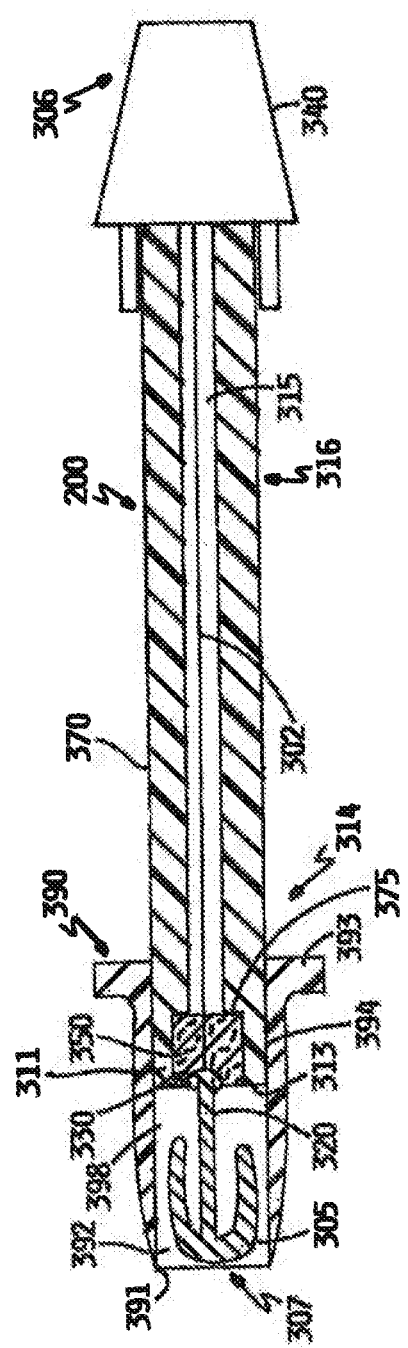
FIG. 13 is a side view of a tissue puncture closure device, with one type of bypass device, according to one aspect of the disclosure.

Referring now to FIG. 13, a tissue puncture closure device 200, for example, a vascular closure device, is shown according to one embodiment of the disclosure. The tissue puncture closure device 200 has a first or proximal end 306 and a second or distal end 307. The tissue puncture closure device 200 includes a closure device cap 340 disposed at the proximal end 306 of the tissue puncture closure device 200, wherein the closure device cap 340 is coupled to the proximal end of a carrier tube 370. The closure device cap 340 may take on a variety of shapes, one such shape for the closure device cap 340 depicted in FIG. 13. Generally, the tissue puncture closure device 200 is inserted into an introducer or insertion sheath 380, the distal end of the introducer or insertion sheath 380 inserted through a puncture tract 410 in a tissue layer and into a lumen 400. The proximal end of the insertion sheath 380 may include a hemostatic valve disposed within an insertion sheath cap 384 (See FIG. 19), through which the distal end of the tissue puncture closure device 200 is inserted. As the tissue puncture closure device 200 is inserted into the introducer or insertion sheath 380, the insertion sheath cap 384 will engage with the tissue puncture closure device cap 340. Hence the insertion sheath cap 384 and the closure device cap 340 are configured to be complementary.

As shown in FIG. 13, the carrier tube 370 extends from the proximal end portion 306 to the distal end portion 307 of the tissue puncture closure device 200, and includes an outlet 313 at the distal end 311 of the carrier tube 370. The carrier tube 370 includes a bypass device 390 disposed at the distal end 311 of the carrier tube 370. The bypass device 390 may be, for example, a bypass tube 398, and may be disposed at the distal end 311 of the carrier tube 370 such that the exterior of the distal end 311 of the carrier tube 370 is disposed within the interior lumen of the proximal end 394 of the bypass tube 398. The anchor 305 is disposed adjacent the distal end 311 of the carrier tube 370, but not within the lumen 315 of the carrier tube 370. Thus, the anchor 305, in one embodiment, is disposed adjacent the distal end 311 of the carrier tube 370, but outside of the lumen 315 of the carrier tube 370. The anchor 305, instead, may be disposed in the lumen 392 of the bypass tube 398, in the chamber formed by and between the distal end 391 of the bypass tube 398 and the distal end 311 of the carrier tube 370. The anchor 305 may be maintained in the lumen 392 of the bypass tube 398 in a bent, folded or collapsed state, ready to be deployed. In an alternative configuration, as described below, the anchor 305 may be maintained in an unfolded state, also ready to be deployed. The distal end 391 of the bypass tube 398 is open-ended, as expected of a tube, and the compressive force exerted by the bypass tube 398 upon the anchor 305 maintains the anchor 305 in place in the chamber formed between the distal end 311 of the carrier tube 370 and the distal end 391 of the bypass tube 398.

Figure 14:
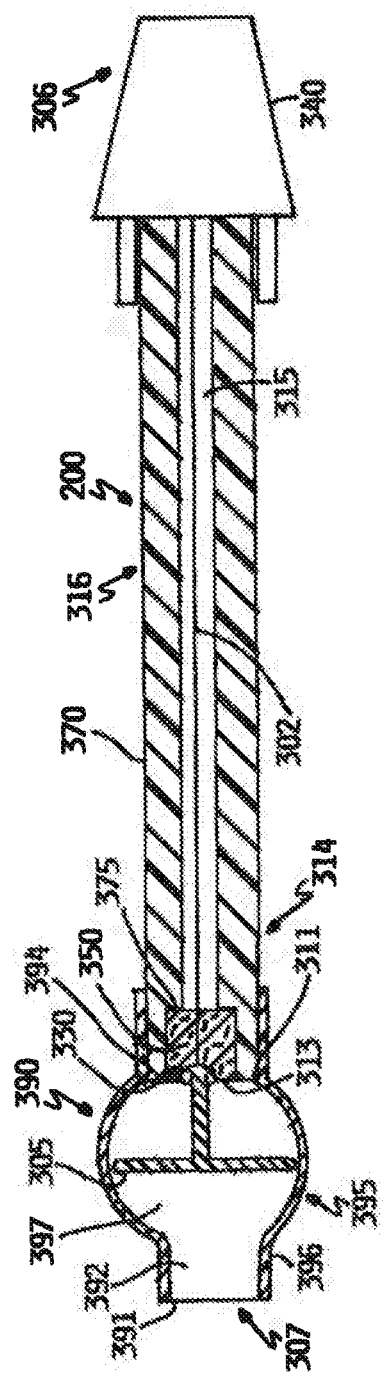
FIG. 14 is a side view of a tissue puncture closure device, with one type of bypass device, according to one aspect of the disclosure.

In another embodiment, as shown is FIG. 14, the carrier tube 370 includes a bypass device 390 disposed at the distal end 311 of the carrier tube 370. The bypass device 390 shown in the embodiment in FIG. 14 is a bypass tube 396 with an integral bulbous portion 395, wherein the bulbous portion 395 is disposed along a length of the bypass tube 396. The diameter of the bulbous portion 395 of the bypass tube 396 is larger than the diameter of the other tubular portions of the bypass tube 396. The bypass device 390 may be disposed at the distal end 311 of the carrier tube 370 such that the exterior of the distal end 311 of the carrier tube 370 is disposed within the interior lumen of the proximal end 394 of the bypass tube 396. The anchor 305 may be disposed near the distal end 311 of the carrier tube 370, but not within the lumen 315 of the carrier tube 370. Thus, the anchor 305, in this embodiment, may be disposed near the distal end 311 of the carrier tube 370, but outside of the lumen 315 of the carrier tube 370. The anchor 305, instead, may be disposed in the lumen 397 of the bulbous portion 395 of the bypass device 390. The anchor 305 may be maintained in the lumen 397 of the bulbous portion 395 of the bypass device 390 in an unfolded, or fully extended state, also ready to be deployed. The distal end 391 of the bypass device 390 is open-ended, as expected of a bypass tube 396, and the compressive force exerted by the non-bulbous portion of the bypass tube 396 upon the anchor 305, as the carrier tube 370 travels through the bypass device 390 causes the anchor 305 to fold, bend, or collapse. Thus, as the tissue puncture closure device 200 is inserted into an insertion sheath 380, the entire bypass device 390 will not travel through an internal passage of the insertion sheath 380, as at least the diameter of the bulbous portion 395 of the bypass device 390 is greater than the diameter of the insertion sheath 380, and will not pass through. Therefore, as the tissue puncture closure device 200 is inserted into the insertion sheath 380, the bulbous portion 395 of the bypass device 390 bears against a surface 382 of the insertion sheath 380. Further insertion of the tissue puncture closure device 200 results in a sliding movement between the carrier tube 370 and the bypass device 390, causing the anchor 305 to bend, fold, or collapse, such that the anchor 305 and the carrier tube 370 may pass through the internal passage of the insertion sheath 380. The anchor 305 remains in a generally folded or bent arrangement following release from the bypass device 390 as the insertion sheath 380 continues to confine the anchor 305 in a folded or bent configuration within the lumen of the insertion sheath 380. As the tissue puncture closure device 200 is inserted further into the insertion sheath 380, the tissue puncture closure device 200 passes through the insertion sheath 380 until the tissue puncture closure device 200 engages with or snaps together with the insertion sheath cap 384. The anchor 305 unbends or unfolds to generally its original shape when the anchor 305 exits the distal end 311 of the carrier tube 370 and enters the tissue or blood vessel lumen.

The sealing plug 350 is disposed within the distal end portion 314 of the carrier tube 370. The carrier tube 370 includes a stop, for example, a lip, shoulder or stop 375, emanating from the interior wall of the distal end portion 314 of the carrier tube 370. The stop 375 may take the form of an annular lip or, alternatively, the stop 375 may take the form of an annular lip with at least one or a plurality of segments removed from around the lip, or some other obstructive structure emanating from the interior wall of the distal end portion 314 of the carrier tube 370, yet leaving a central lumen 315 of the carrier tube 370 unobstructed. Alternatively, the stop 375 may form a shoulder from a thickened interior wall extending from a section of the distal end portion 314 of the carrier tube 370 to the proximal end portion 316 of the carrier tube 370, resulting in a smaller diameter central lumen 315 of the carrier tube 370. The stop 375 is configured to hold and maintain the sealing plug 350 in place in the distal end portion 314 of the carrier tube 370. The stop 375 forms a cavity in the distal end portion 314 of the carrier tube 370, configured to accommodate the sealing plug 350, prior to deployment of the sealing plug 350. Further, the stop 375 forms a barrier preventing the sealing plug 350 from traveling proximally within the lumen 315 of the carrier tube 370.

Figure 15:
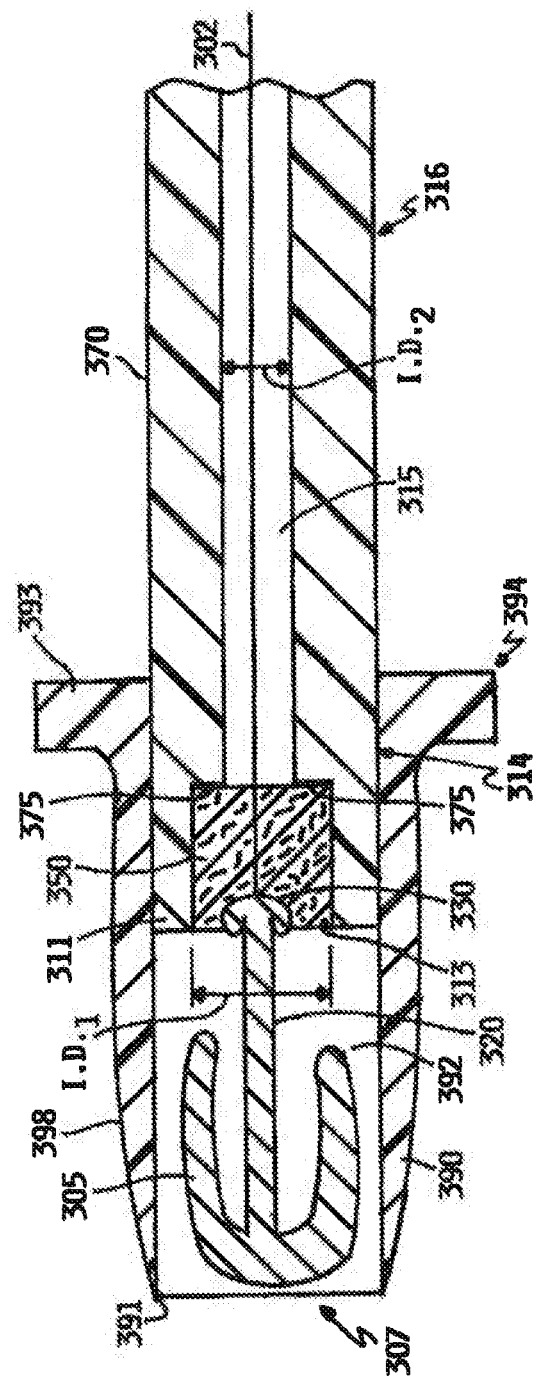
FIG. 15 is a side view of the distal portion of a tissue puncture closure device, according to one aspect of the disclosure.
Figure 16:
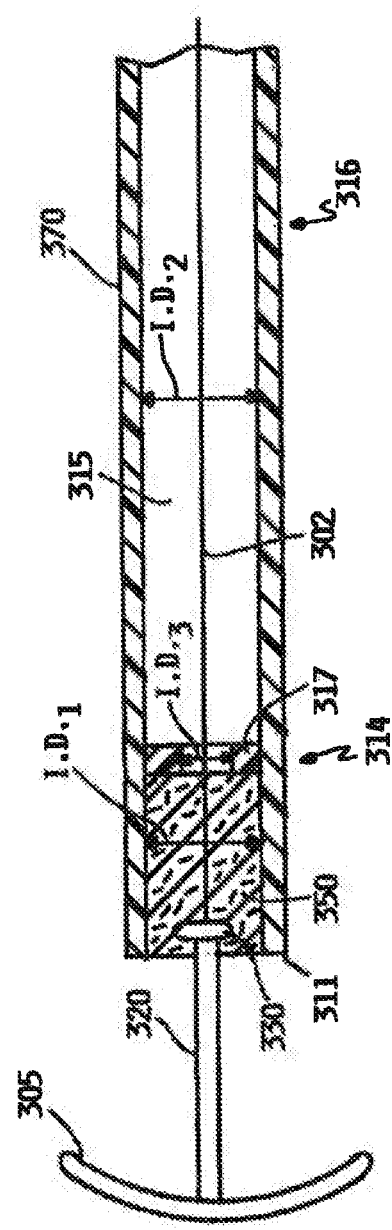
FIG. 16 is a side view of a distal portion of a carrier tube, with the anchor deployed, according to one embodiment of the disclosure.

In one embodiment, as shown in FIG. 15, the carrier tube lumen 315 has an inner diameter I.D.1 at the distal end 311 of the carrier tube 370 that is larger than the inner diameter I.D.2 of the lumen 315 in the proximal end portion 316 of the carrier tube 370, where the inner diameter I.D.2 proceeds proximally generally from the location of the proximal end of the sealing plug 350 and from the stop 375 formed in the distal end portion 314 of the carrier tube 370. FIG. 15 shows an example of the above structure, wherein the lumen 315 inner diameter I.D.1 at the distal end portion 314 of the carrier tube 370 is larger than the lumen 315 inner diameter I.D.2 of the proximal end portion 316 of the carrier tube 370. In another embodiment, as shown in FIG. 16, an annular ring 317 is positioned in the lumen 315 of the carrier tube 370, in the distal end portion 314 of the carrier tube 370. Thus, the annular ring 317 restricts the movement of the sealing plug 350 proximally in the lumen 315 of the carrier tube 370. However, the inner diameter I.D.1 of the distal end portion 314 of the carrier tube 370 is substantially the same as the inner diameter I.D.2 of the proximal end portion 316 of the carrier tube 370, except at the position of the annular ring 317. The diameter I.D.3 of the aperture of the annular ring 317 is smaller than the inner diameter I.D.1 of the distal end portion 314 of the carrier tube 370 or the inner diameter I.D.2 of the proximal end portion 316 of the carrier tube 370.

As noted above and shown in FIGS. 7-15, an anchor assembly 300 includes the anchor 305, an anchor shaft 320 and a boss 330 structure at the proximal end of the anchor shaft 320. Further, a filament, suture or thread 302 is attached to the anchor shaft 320 of the anchor 305. The term suture 302 is used hereinafter to encompass other like structures, for example, a thread or filament. The suture 302 is coupled to the anchor shaft 320 by, for example, being tied to the anchor shaft 320, being molded into the anchor shaft 320, or the like. In one embodiment, the suture 302 exits the anchor shaft 320 through the top surface of the boss 330. The suture 302 may be threaded through one or more perforations in the sealing plug 350, and proximally back toward the proximal end portion 316 of the carrier tube 370 and to the closure device cap 340. The suture 302 may also be threaded around itself to form a self-tightening slip-knot. The suture 302 thus connects the anchor assembly 300 and the sealing plug 350. The proximal end of the anchor assembly 300, the boss 330, may be disposed adjacent the distal end of the sealing plug 350, as the sealing plug 350 is disposed in the distal end portion 314 of the carrier tube 370. Alternatively, as shown, for example, in FIGS. 13 and 15, the boss 330 may be disposed within the distal end portion of the sealing plug 350. The proximal end of the suture 302 is attached to a release mechanism within the closure device cap 340, and the tension of the suture 302 assists in maintaining the relative positions of the anchor assembly 300 and the sealing plug 350, with the stop 375 restricting proximal movement of the sealing plug 350 within the lumen 315 of the carrier tube 370.

Figure 17:
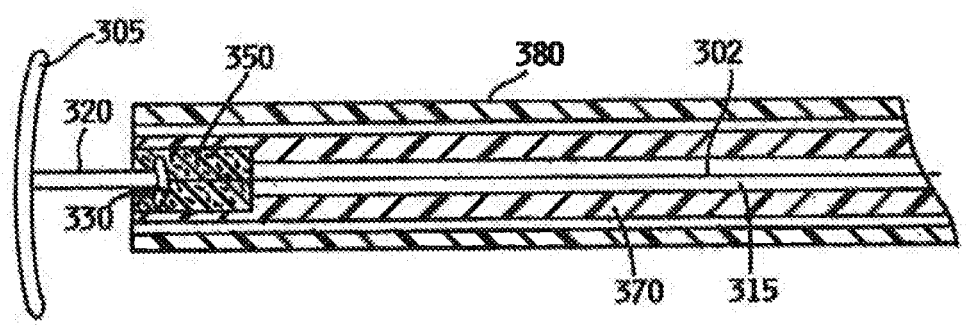
FIG. 17 is a side view of a distal portion of a carrier tube in an insertion sheath, according to one embodiment of the disclosure.
Figure 18:
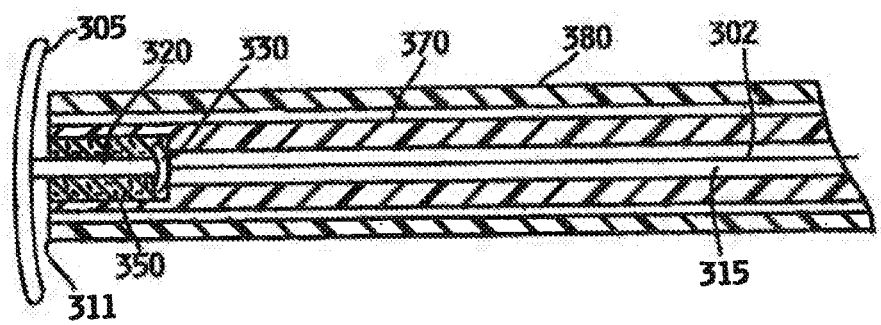
FIG. 18 is a side view of a distal portion of a carrier tube, with the anchor shaft having largely traveled proximally through the sealing plug material, according to one embodiment of the disclosure.

When the bypass device 390 is removed from the distal end 311 of the carrier tube 370 during operation, the closure device cap 340 is manipulated to create sufficient tension on the suture 302 such that the anchor shaft 320 is drawn proximally, through the sealing plug 350 material. FIG. 17 shows the beginnings of this cycle, as the tension on the suture 302 is increased, thereby causing the anchor shaft 320 to begin to travel proximally through the sealing plug 350 material. FIG. 18 shows the anchor shaft 320 having traveled further proximally through the sealing plug 350 material, with the anchor 305 in the position it would be in, disposed against the interior wall of the tissue lumen; against the interior wall of the vessel lumen. FIG. 12 shows the anchor 305 in place against the inner puncture wall, for example, the anchor 305 against the inner wall of a blood vessel, with the anchor shaft 320 having traveled proximally such that the boss 330 is positioned on the proximal side of the of the sealing plug 350 and holds the sealing plug 350 in place, proximally.

In operation, a locator may be used with an insertion sheath 380, wherein the locator is inserted into the insertion sheath 380. In one method, a guidewire is inserted into a procedure sheath that is in the patient, and then the procedure sheath is removed, leaving the guidewire in place to maintain access to the tissue puncture, for example, to maintain vascular access. The locator/insertion sheath assembly is threaded over the guidewire and inserted into the puncture tract. Blood will begin to drip from a drip hole in the locator, indicating that the tip of the insertion sheath 380 is within the vessel. The locator/insertion sheath assembly is withdrawn until the blood slows or stops flowing from the drip hole, indicating that the distal locator holes of the insertion sheath 380 have just exited the artery. The locator/insertion sheath assembly is advanced until blood begins to drip from the drip hole in the locator, and the locator and guidewire are then removed from the insertion sheath 380. The tissue puncture closure device 200 is then inserted into the insertion sheath 380. The above procedure may also be conducted without the use of a guidewire.

Figure 19:
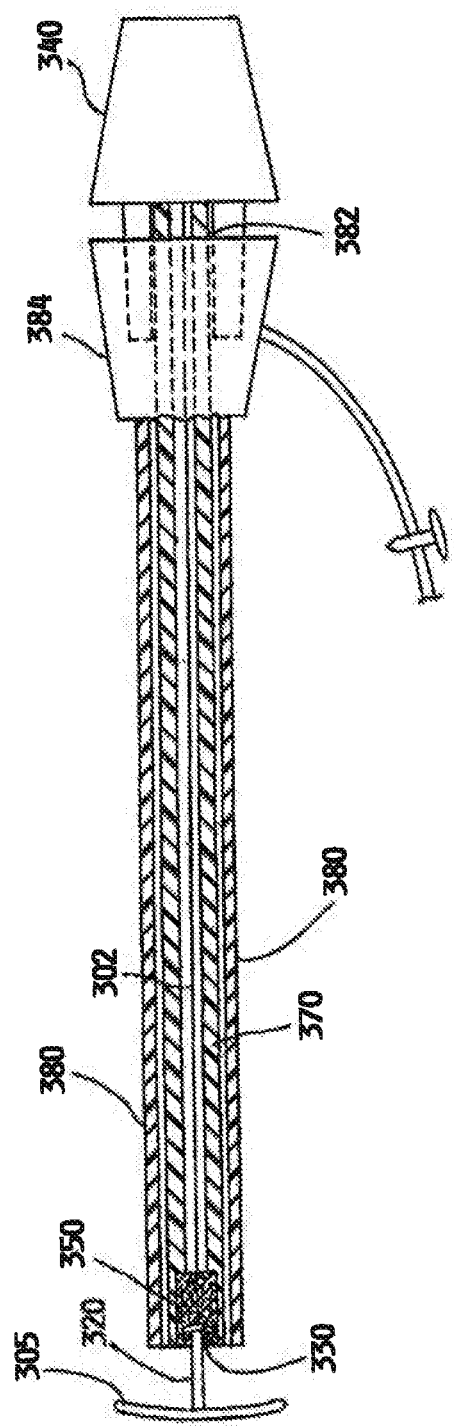
FIG. 19 is a view of a tissue puncture closure device inserted into an insertion sheath, according to one embodiment of the disclosure.

Referring now to FIGS. 15 and 19, FIG. 19 shows the tissue puncture closure device 200 inserted into an introducer or insertion sheath 380. As noted above, the carrier tube 370 includes a bypass device 390 disposed at the distal end 311 of the carrier tube 370. The bypass device 390 may be, for example, a bypass tube 398 or bypass tube 396 with a bulbous portion 395, and may be disposed at the distal end 311 of the carrier tube 370 such that the exterior of the distal end 311 of the carrier tube 370 is disposed within the interior lumen 392 of the proximal end 394 of the bypass device 390. The bypass tube 398 includes an oversized head 393 that prevents the bypass tube 398 from passing through the lumen of the insertion sheath 380. Therefore, as the tissue puncture closure device 200 is inserted into the insertion sheath 380, the oversized head 393 bears against a surface 382 of the insertion sheath 380. Further insertion of the tissue puncture closure device 200 results in a sliding movement between the carrier tube 370 and the bypass tube 398, releasing the anchor 305 from the bypass tube 398. However, the anchor 305 remains in the generally folded or bent arrangement shown in FIG. 13 or FIG. 15 following release from the bypass tube 398 as the insertion sheath 380 continues to limit the ability of the anchor 305 to unfold or unbend. As the tissue puncture closure device 200 is inserted further into the insertion sheath 380, the tissue puncture closure device 200 passes through the insertion sheath 380 until the tissue puncture closure device 200 engages with or snaps together with the insertion sheath cap 384. If there was a disparity in the lengths of the insertion sheath 380 and the tissue puncture closure device 200, an adapter may be added to the proximal end of the insertion sheath 380, to obtain the needed length, such that the tissue puncture closure device 200 and the insertion sheath 380 engage properly and the anchor 305 is ejected and is disposed at the distal end 311 of the carrier tube (FIGS. 12, 18 and 19), adjacent the interior wall of the tissue puncture or arteriotomy. The bypass device 390 with the bulbous portion 395 performs similarly to the bypass tube 398; the bulbous portion 395 of the bypass tube 396 prevents the bypass tube 396 from passing through the lumen 315 of the insertion sheath 380. Therefore, as the tissue puncture closure device 200 is inserted into the insertion sheath 380, the bulbous portion 395 bears against a surface 382 of the insertion sheath 380. Further insertion of the tissue puncture closure device 200 results in a sliding movement between the carrier tube 370 and the bypass tube 396, releasing the anchor 305 from the bypass tube 396. However, the anchor 305 becomes folded or bent as it travels from an extended configuration in the bulbous portion 395 of the bypass tube 396, and enters the distal end of the bypass tube 396 and on into the insertion sheath 380. When the tissue puncture closure device 200 and the insertion sheath 380 engage properly, as noted above, the anchor 305 is ejected and is disposed at the distal end 311 of the carrier tube (FIGS. 12, 18 and 19), adjacent the interior wall of the tissue puncture or arteriotomy. The anchor 305 in the bypass device 390 with the bulbous portion 395 is not in a bent or folded configuration for as long a time, generally, as an anchor 305 in the bypass tube 398. However, the anchor 305, in either instance, generally has shape memory to return to the extended or unfolded configuration.

Figure 20:
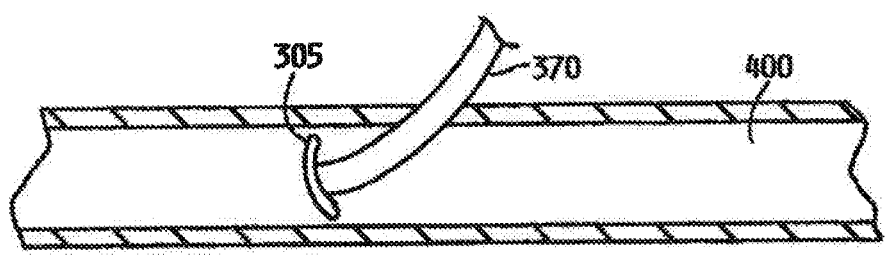
FIG. 20 is a side view of an anchor deployed in a lumen, the anchor adjacent the distal end of a carrier tube, according to one embodiment of the disclosure.
Figure 21:
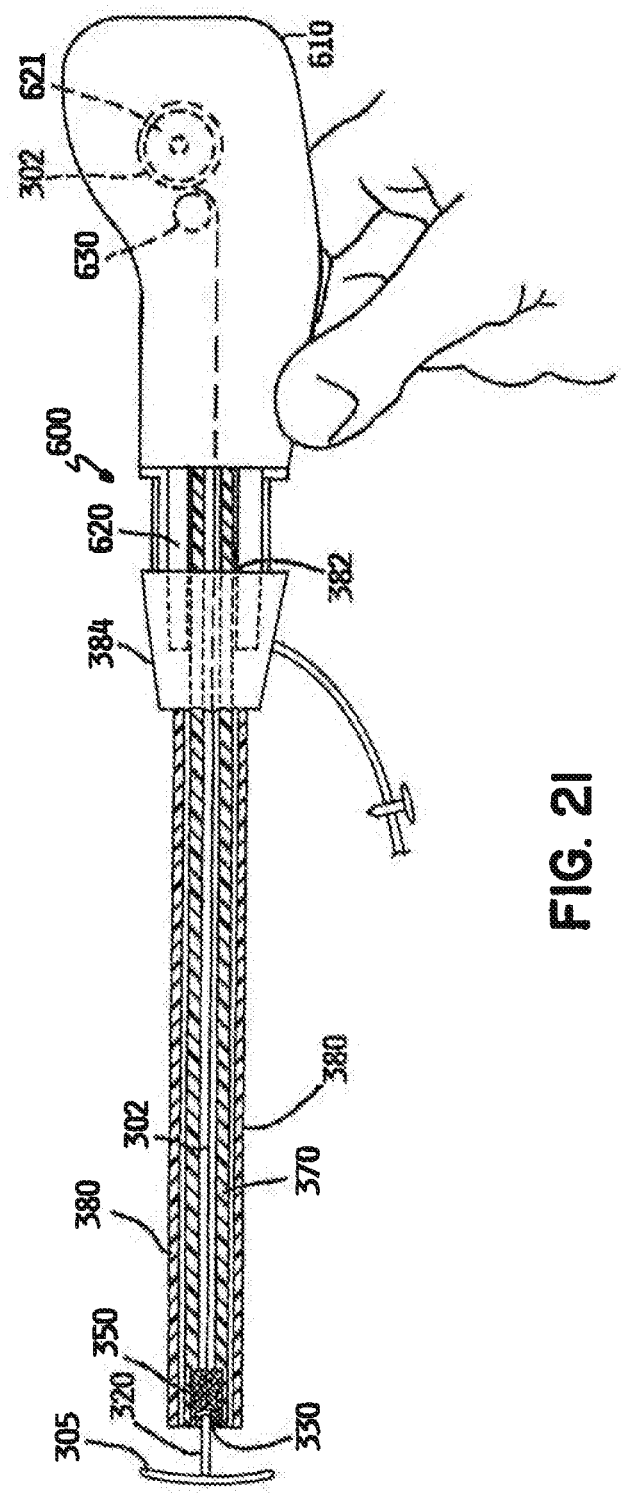
FIG. 21 is a view of a tissue puncture closure device inserted into an insertion sheath, according to one embodiment of the disclosure.

Once the insertion sheath 380 and the tissue puncture closure device 200 are engaged, the anchor 305 is exposed within the tissue lumen or, for example, the lumen of the blood vessel. Although tissue closure may be effected in various tissue lumen, the example provided as a general example is the closure of a percutaneous incision to the femoral artery, involving the sealing of a puncture in the femoral artery wall. However, other similar tissue closure is contemplated. The anchor 305 returns to its manufactured, extended or unfolded shape to allow the anchor 305 to conform to the inner artery wall. The closure device cap 340 is manipulated to create sufficient tension on the suture 302 to draw the anchor shaft 320 through the sealing plug 350 material, such that the anchor boss 330 is pulled proximally through the sealing plug 350 material and is positioned proximate the sealing plug 350, and to set the anchor 305 on the distal end 311 of the carrier tube 370 in a position to catch on the arteriotomy (see FIGS. 12 and 20), to be disposed adjacent the interior wall of the arteriotomy, in the artery lumen. Once the anchor 305 is disposed in position adjacent the interior wall of the artery lumen, and the anchor shaft 320 and boss 330 have been pulled through the sealing plug 350 material, the tissue puncture closure device 200 and the insertion sheath 380 are pulled proximally as a unit. The tissue puncture closure device 200 and the insertion sheath 380 are withdrawn out of the puncture tract as one unit, allowing the anchor 305 to catch on the inner arterial wall, ejecting the sealing plug 350 out of the distal end 311 of the carrier tube 370, disposing the sealing plug 350 in the puncture tract adjacent the exterior of the arteriotomy (see FIG. 12). The puncture closure device cap 340 is manipulated further such that the suture 302 is released, allowing the suture 302 to pull freely out the distal end 311 of the carrier tube 370. Prior to the release of the suture 302, the anchor shaft 320 and boss (knob) 330 have traveled proximally through the sealing plug 350 material and the boss 330 has passed through the proximal surface of the sealing plug 350 material. Thus, the boss 330 holds and maintains the sealing plug 350 in place along the anchor shaft 320, and does not allow the sealing plug 350 to move proximally beyond the boss 330. With the deployment of the anchor 305 and the sealing plug 350, the tissue puncture is sandwiched between the anchor 305 and the sealing plug 350, thereby sealing the puncture. Hemostasis is provided from the inside, the outside and within the tissue puncture, e.g., the arteriotomy. The tissue puncture closure device 200 and the insertion sheath 380 may be completely removed from the puncture tract, once the suture 302 is allowed to pull freely out of the distal end 311 of the carrier tube 370, leaving the anchor 305, anchor shaft 320, and sealing plug 350 in place, with the suture 302 trailing outside the puncture tract, outside the body. The suture 302 allows for the potential retrieval of the anchor 305 and/or sealing plug 350, and keeps the anchor 305/sealing plug 350 from traveling downstream within the artery. Once hemostasis is achieved, the suture 302 may be cut below skin level. The suture 302 is cut and the incision tract 410 may be closed.

Alternatively, the tissue puncture closure device 600 may use the anchor assemblies 300, as described above, as well as the carrier tube 370/bypass devices 390 described above with a different handle configuration. Instead of a closure device cap 340, the proximal end of the carrier tube 370 is coupled to a housing 610. Disposed at the distal end of the housing 610 is an attachment mechanism 620, for example, a set of prongs 620 or the like, whereby the housing 610 may be engaged with an insertion sheath cap 384. The tissue puncture closure device 600, in operation, is somewhat similar to the tissue puncture closure device 200 described above. Once the insertion sheath 380 and the tissue puncture closure device 600 are engaged, the anchor 305 is exposed within the tissue lumen or, for example, the lumen of the blood vessel. The anchor 305 returns to its unfolded shape to allow the anchor 305 to conform to the inner artery wall. The tissue puncture closure device 600 may be pulled proximally, relative to the insertion sheath cap 384, thus coupling the tissue puncture closure device 600 to the insertion sheath cap 384, and thereby drawing the anchor shaft 320 through the sealing plug 350 material, such that the anchor boss 330 is pulled proximally through the sealing plug 350 material and is disposed proximate the sealing plug 350, and the anchor 305 is set on the distal end 311 of the carrier tube 370 in a position to catch on the arteriotomy (see FIGS. 12 and 20), disposed adjacent the interior wall of the arteriotomy, in the artery lumen. The boss 330 holds and maintains the sealing plug 350 in place along the anchor shaft 320, and does not allow the sealing plug 350 to move proximally beyond the boss 330. Once the anchor 305 is disposed in position adjacent the interior wall of the artery lumen, and the anchor shaft 320 and boss 330 have been pulled through the sealing plug 350 material, the tissue puncture closure device 600 and the insertion sheath 380 are pulled proximally as a unit. The tissue puncture closure device 600 and the insertion sheath 380 are withdrawn out of the puncture tract as one unit, allowing the anchor 305 to catch on the inner arterial wall, ejecting the sealing plug 350 out of the distal end 311 of the carrier tube 370, disposing the sealing plug 350 in the puncture tract adjacent the exterior of the arteriotomy (see FIG. 12). The suture 302, meanwhile, has been unwinding from a spool 621 or the like, disposed in the housing 610. A button release 630, or other release mechanism, is actuated such that the suture 302 is allowed to pull freely out the distal end 311 of the carrier tube 370. With the deployment of the anchor 305 and the sealing plug 350, the tissue puncture is sandwiched between the anchor 305 and the sealing plug 350, thereby sealing the puncture. Hemostasis is provided from the inside, the outside and within the tissue puncture, e.g., the arteriotomy.

Once hemostasis is achieved, the suture 302 may be cut below skin level. The suture 302 is cut and the incision tract 410 may be closed.

The suture 302, anchor 305, anchor shaft 320, and sealing plug 350 are generally made of biocompatible resorbable materials, and remain in place while the tissue puncture 420 heals, until the resorbable materials eventually resorb into the body. By varying the materials that compose the anchor 305, anchor shaft 320, boss 330, and sealing plug 350, the resorbability rate of the particular closure component may be controlled, such that, for example, the anchor 305 may resorb very quickly, leaving the anchor shaft 320, boss 330, and sealing plug 350, or just the sealing plug 350, in place to maintain hemostasis. Thus hemostasis may be maintained without an anchor 305 being present in the artery lumen, or other tissue lumen. Further, with the configuration of the anchor shaft 320, boss 330 and sealing plug 350 material fixed on the anchor shaft 320, there is no need for a tamping device or additional tamping to dispose the sealing plug 350 in place adjacent the outer surface of the tissue puncture or arteriotomy.

The preceding description has been presented only to illustrate and describe example embodiments of disclosure. It is not intended to be exhaustive or to limit the disclosure to any precise form disclosed. Many modifications and variations are possible in light of the above teaching. Although specific examples have been illustrated and described herein, it will be appreciated by those of ordinary skill in the art that any arrangement calculated to achieve the same purpose could be substituted for the specific examples shown. This application is intended to cover adaptations or variations of the present subject matter. Therefore, it is intended that the disclosure be defined by the attached claims and their legal equivalents.

What is claimed is:

1. An anchor assembly for sealing a tissue puncture, the anchor assembly comprising a flexible anchor, an anchor shaft configured to receive a sealing plug made of a bioresorbable material so that the anchor shaft passes through the sealing plug, and a boss, the anchor shaft possessing a distal-most end and a proximal-most end, the flexible anchor being fixedly disposed at the distal-most end of the anchor shaft so that the flexible anchor is positionally fixed with respect to the distal-most end of the anchor shaft, the boss being fixedly disposed at the proximal-most end of the anchor shaft so that the boss is positionally fixed with respect to the proximal-most end of the anchor shaft, the anchor comprising a bioresorbable material that resorbs more rapidly than a bioresorbable material composing the anchor shaft and a bioresorbable material composing the boss, the flexible anchor being a flexible low profile body that is bendable or foldable to be positioned inside a deployment device for delivery to a location of the tissue puncture.

2. The anchor assembly of claim 1, wherein the anchor assembly is connectable to the sealing plug by a filament, the sealing plug and the filament being made of at least one bioresorbable material.

3. The anchor assembly of claim 2, wherein the anchor bioresorbable material resorbs more rapidly than the sealing plug and filament bioresorbable material.

4. The anchor assembly of claim 1, wherein the flexible anchor that is bendable or foldable to be positioned inside the deployment device for delivery to the location of the tissue puncture comprises at least one flexible rib.

5. An anchor assembly for sealing a tissue puncture, the anchor assembly comprising:
an anchor,
an anchor shaft configured to receive a sealing plug made of a bioresorbable material so that the anchor shaft passes through the sealing plug, the anchor shaft possessing a distal-most end and a proximal-most end, and
a boss,
the anchor being fixed to the distal-most end of the anchor shaft so that the anchor is positionally fixed with respect to the distal-most end of the anchor shaft and the boss being fixed to the proximal-most end of the anchor shaft so that the boss is positionally fixed with respect to the proximal-most end of the anchor shaft,
wherein the anchor comprises a bioresorbable material that resorbs more rapidly than a bioresorbable material composing the anchor shaft and a bioresorbable material composing the boss,
the anchor including a surface distal to the distal-most end of the anchor shaft and at least one rib on the surface, and
the anchor together with the at least one rib being a flexible low profile body that is bendable or foldable to be positioned inside a deployment device for delivery to a location of the tissue puncture.

6. The anchor assembly of claim 5, wherein the at least one rib comprises a plurality of ribs equidistantly spaced about the anchor.

7. The anchor assembly of claim 5, wherein the anchor shaft is integrally formed with the anchor.

8. The anchor assembly of claim 5, wherein the anchor shaft is semi-flexible.

9. The anchor assembly of claim 5, wherein the boss is semi-flexible.

10. The anchor assembly of claim 5, wherein the anchor shaft is fixedly coupled with the anchor.

11. The anchor assembly of claim 5, wherein the anchor defines a first cross-sectional area, the anchor shaft defines a second cross-sectional area, and the boss defines a third cross-sectional area, the first cross-sectional area being greater than the second cross-sectional area and the third cross-sectional area being greater than the second cross-sectional area.

12. The anchor assembly of claim 1, wherein the anchor defines a first cross-sectional area, the anchor shaft defines a second cross-sectional area, and the boss defines a third cross-sectional area, the first cross-sectional area being greater than the second cross-sectional area and the third cross-sectional area being greater than the second cross-sectional area.

* * * * *